(12) United States Patent
Chen et al.

(10) Patent No.: US 11,564,640 B2
(45) Date of Patent: Jan. 31, 2023

(54) BLOOD PRESSURE MEASUREMENT METHOD, BLOOD PRESSURE MEASUREMENT APPARATUS, AND TERMINAL

(71) Applicant: HUAWEI TECHNOLOGIES CO., LTD., Guangdong (CN)

(72) Inventors: Wenjuan Chen, Shenzhen (CN); Yu Zhu, Shenzhen (CN)

(73) Assignee: Huawei Technologies Co., Ltd., Shenzhen (CN)

( * ) Notice: Subject to any disclaimer, the term of this patent is extended or adjusted under 35 U.S.C. 154(b) by 1195 days.

(21) Appl. No.: 15/762,640

(22) PCT Filed: Sep. 25, 2015

(86) PCT No.: PCT/CN2015/090808
§ 371 (c)(1),
(2) Date: Mar. 23, 2018

(87) PCT Pub. No.: WO2017/049624
PCT Pub. Date: Mar. 30, 2017

(65) Prior Publication Data
US 2018/0263570 A1 Sep. 20, 2018

(51) Int. Cl.
*A61B 5/00* (2006.01)
*A61B 5/021* (2006.01)
(Continued)

(52) U.S. Cl.
CPC ............ *A61B 5/7278* (2013.01); *A61B 5/021* (2013.01); *A61B 5/1116* (2013.01);
(Continued)

(58) Field of Classification Search
None
See application file for complete search history.

(56) References Cited

U.S. PATENT DOCUMENTS 9,017,368 B2 * 4/2015 Usuda ................ A61B 5/02116
600/300
2007/0055163 A1 3/2007 Asada et al.
(Continued)

FOREIGN PATENT DOCUMENTS

CN 102462492 A 5/2012
CN 103845046 A 6/2014
(Continued)

OTHER PUBLICATIONS

Wei et al. A New Wristband Wearable Sensor Using Adaptive Reduction Filter to Reduce Motion Artifact; 2008; Proceedings of the 5th International Conference on Information Technology and Application in Biomedicine (Year: 2008).*
(Continued)

*Primary Examiner* — Jay B Shah
(74) *Attorney, Agent, or Firm* — Fish & Richardson P.C.

(57) ABSTRACT

Embodiment provides a terminal which comprises at least one processor. The at least one processor is configured to: obtain first biometric feature information of a measured target, where the first biometric feature information includes a pulse wave signal and/or an electrocardio signal of the measured target; obtain a first status of the measured target according to the first biometric feature information of the measured target; determine blood pressure calculation policy of the measured target according to the first status of the measured target; and determine a blood pressure value of the measured target according to the blood pressure calculation policy and the first biometric feature information of the measured target.

23 Claims, 10 Drawing Sheets

(51) Int. Cl.
*A61B 5/11* (2006.01)
*A61B 5/322* (2021.01)
*A61B 5/318* (2021.01)
*A61B 5/0205* (2006.01)
*A61B 5/0255* (2006.01)

(52) U.S. Cl.
CPC ............ *A61B 5/1118* (2013.01); *A61B 5/322* (2021.01); *A61B 5/0205* (2013.01); *A61B 5/0255* (2013.01); *A61B 5/318* (2021.01); *A61B 2560/0228* (2013.01); *A61B 2562/0219* (2013.01)

(56) References Cited

U.S. PATENT DOCUMENTS

| | | | |
|---|---|---|---|
| 2007/0066910 A1 | 3/2007 | Inukai et al. | |
| 2010/0049059 A1 | 2/2010 | Ha et al. | |
| 2010/0081946 A1* | 4/2010 | Garudadri | A61B 5/7221 600/485 |
| 2013/0018272 A1* | 1/2013 | Hori | A61B 5/021 600/501 |
| 2014/0012147 A1* | 1/2014 | Li | A61B 5/022 600/494 |
| 2014/0155767 A1 | 6/2014 | Fukuda et al. | |
| 2014/0288445 A1* | 9/2014 | Makkonen | A61B 5/02108 600/490 |

FOREIGN PATENT DOCUMENTS

| | | |
|---|---|---|
| CN | 103892816 A | 7/2014 |
| CN | 104138253 A | 11/2014 |
| CN | 104665794 A | 6/2015 |
| CN | 104706348 A | 6/2015 |

OTHER PUBLICATIONS

Chan et al. Noninvasive and Cuffless Measurements of Blood Pressure for Telemedicine 2001 Proceedings of the 23rd Annual EMBS International Conference, Oct. 25-28, Istanbul, Turkey (Year: 2001).*
International Search Report issued in International Application No. PCT/CN2015/090808 dated Feb. 25, 2016, 20 pages.
Extended European Search Report issued in European Application No. 15904500.4 dated Jun. 26, 2018, 7 pages.
Office Action issued in Chinese Application No. 201580029168.8 dated Jul. 31, 2019, 10 pages.
Communication pursuant to Article 94(3) EPC issued in European Application No. 15904500.4 dated Apr. 3, 2019, 7 pages.

* cited by examiner

BLOOD PRESSURE MEASUREMENT METHOD, BLOOD PRESSURE MEASUREMENT APPARATUS, AND TERMINAL

CROSS-REFERENCE TO RELATED APPLICATIONS

This application is a national stage of International Application No. PCT/CN2015/090808 filed on Sep. 25, 2015, which is hereby incorporated by reference in its entirety

TECHNICAL FIELD

The present invention relates to the field of measurement, and in particular, to a blood pressure measurement method, a blood pressure measurement apparatus, and a terminal.

BACKGROUND

High blood pressure is a common cardiovascular disease, and regularly measuring blood pressure is one of important means to ensure health of patients with high blood pressure. A blood pressure detection apparatus is also referred to as a blood pressure meter. Generally, the blood pressure meter is classified into a cuff blood pressure meter and a cuff-less blood pressure meter. Precision for the cuff blood pressure meter is relatively high, but the cuff blood pressure meter has a big volume, is not readily portable, and is operated complexly. Therefore, the cuff-less blood pressure meter is a main development direction of the blood pressure detection apparatus in recent years.

The cuff-less blood pressure meter determines blood pressure according to a relationship between the blood pressure and a pulse wave. Specifically, a speed at which a pulse wave is transmitted along arteries is in positive correlation with artery blood pressure. When the blood pressure increases, blood vessels dilate, and the transmission speed of the pulse wave increases. In contrast, when the blood pressure decreases, the transmission speed of the pulse wave decreases. In addition, the transmission speed of the pulse wave is also related to a physiological parameter such as age, elasticity of the artery wall, or blood density of a measured person, and physiological parameters of different measured persons are different. Therefore, when blood pressure is obtained by using a transmission speed of a pulse wave, calibration needs to be performed for each measured person.

A method for calibrating a cuff-less blood pressure meter is divided into two manners: manual calibration and automatic calibration. The manual calibration is to calibrate a measurement result of the cuff-less blood pressure meter by using a measurement result of a cuff blood pressure meter. The method for manually calibrating a blood pressure meter is complex, and a physiological parameter of a measured person changes in real time. Therefore, precision for the cuff-less blood pressure meter is still not high. The automatic calibration is to automatically correct an original measurement value according to vascular resistance, elasticity of the vessel artery wall, and blood viscosity, so as to obtain a more precise blood pressure value.

However, blood pressure varies with different measured parts and different postures of a measured person. For example, arteries of a right hand are from a first major branch of an aortic arch, and arteries of a left hand are from a third branch of the aortic arch. Generally, a difference between blood pressure values of the left arm and the right arm of a person is 10-20 mmHg. For a patient with high blood pressure, as a cardiovascular function declines, the difference between blood pressure values of the left arm and the right arm may be higher. Impact of a posture on blood pressure is from gravity. When a person is lying, systolic blood pressure increases. When a person is sitting, systolic blood pressure decreases; whereas, diastolic blood pressure of a person when standing is greater than diastolic blood pressure of the person when lying.

For the existing method for calibrating a cuff-less blood pressure meter, the foregoing impact of different measured parts and different postures of a measured person on blood pressure measurement values is not considered. Therefore, the precision for the cuff-less blood pressure meter is still not high.

SUMMARY

In view of this, an objective of embodiments of the present invention is to provide a blood pressure measurement method, a blood pressure measurement apparatus, and a terminal, so as to resolve a problem in the prior art that precision of a detection result of a cuff-less blood pressure meter is not high.

To resolve the foregoing technical problem, the embodiments of the present invention disclose the following technical solutions:

According to a first aspect, a blood pressure measurement method is provided, where the method includes:

obtaining, by a terminal, first biometric feature information of a measured target, where the first biometric feature information includes a pulse wave signal and/or an electrocardio signal of the measured target;

obtaining, by the terminal, a first status of the measured target according to the first biometric feature information, where the first status includes at least one of an activity status of the measured target, a posture of the measured target, or a measurement location of a pulse wave of the measured target;

determining, by the terminal, a blood pressure calculation policy of the measured target according to the first status; and determining, by the terminal, a blood pressure value of the measured target according to the blood pressure calculation policy and the first biometric feature information.

With reference to the first aspect, in a first possible implementation manner of the first aspect, the first biometric feature information of the measured target further includes:

an acceleration signal and/or an angular velocity signal of the measured target.

With reference to the first aspect or the first possible implementation manner of the first aspect, in a second possible implementation manner of the first aspect, the determining, by the terminal, a blood pressure calculation policy of the measured target according to the first status specifically includes:

if the terminal is calibrated when the measured target is in the first status, determining that the blood pressure calculation policy of the measured target is a calibrated blood pressure calculation policy; or if the terminal is uncalibrated when the measured target is in the first status, determining that the blood pressure calculation policy of the measured target is an uncalibrated blood pressure calculation policy.

With reference to the second possible implementation manner of the first aspect, in a third possible implementation manner of the first aspect, the determining that the blood pressure calculation policy of the measured target is a calibrated blood pressure calculation policy specifically includes:

determining a calibrated blood pressure calculation model and a calibration parameter corresponding to the first status in the calibrated blood pressure calculation model.

With reference to the third possible implementation manner of the first aspect, in a fourth possible implementation manner of the first aspect, the determining a calibrated blood pressure calculation model is specifically:

determining a first calibrated blood pressure calculation model according to the first status.

With reference to the third possible implementation manner of the first aspect or the fourth possible implementation manner of the first aspect, in a fifth possible implementation manner of the first aspect, the calibrated blood pressure calculation model is:

$$DBP = \frac{SBP_0}{3} + \frac{2DBP_0}{3} + A\ln\left(\frac{PTT_0}{PTT}\right) - \frac{(SBP_0 - DBP_0)}{3}\frac{PTT^2}{PTT_0^2}$$

$$SBP = DBP + (SBP_0 - DBP_0)\frac{PTT_0^2}{PTT^2},$$

where

SBP is systolic blood pressure; DBP is diastolic blood pressure; PTT is a pulse wave transmission time; A is a blood pressure calculation coefficient; and $SBP_0$, $DBP_0$, and $PTT_0$ are calibration parameters in the calibrated blood pressure calculation model.

With reference to any one of the first aspect to the fifth possible implementation manner of the first aspect, in a sixth possible implementation manner of the first aspect, before the obtaining, by a terminal, first biometric feature information of a measured target, the method further includes: calibrating the terminal, where the calibrating the terminal includes:

obtaining, by the terminal, second biometric feature information of the measured target, where the second biometric feature information includes a pulse wave signal and/or an electrocardio signal of the measured target;

obtaining, by the terminal, a second status of the measured target according to the second biometric feature information, where the second status includes at least one of an activity status of the measured target, a posture of the measured target, or a measurement location of a pulse wave of the measured target;

obtaining, by the terminal, a standard blood pressure value when the measured target is in the second status; and determining, by the terminal according to the standard blood pressure value and the second biometric feature information, a calibration parameter corresponding to the second status in the calibrated blood pressure calculation model.

With reference to the second possible implementation manner of the first aspect, in a seventh possible implementation manner of the first aspect, the determining that the blood pressure calculation policy of the measured target is an uncalibrated blood pressure calculation policy specifically includes:

determining an uncalibrated blood pressure calculation model and a body parameter of the measured target, where the body parameter of the measured target includes at least one of age, gender, height, or weight.

With reference to the seventh possible implementation manner of the first aspect, in an eighth possible implementation manner of the first aspect, the uncalibrated blood pressure calculation model is:

$SBP = A_1 \ln PTT + A_2 Age + A_3 Hei + A_4 Wei + A_5 Gen + A_6 \ln Z + A_7$ $DBP = B_1 \ln PTT + B_2 Age + B_3 Hei + B_4 Wei + B_5 Gen + B_6 \ln Z + B_7$, where SBP is systolic blood pressure; DBP is diastolic blood pressure; $A_1$, $A_2$, $A_3$, $A_4$, $A_5$, $A_6$, and $A_7$ are systolic blood pressure calculation coefficients; $B_1$, $B_2$, $B_3$, $B_4$, $B_5$, $B_6$, and $B_7$ are diastolic blood pressure calculation coefficients; PTT is a pulse wave transmission time; Age is the age of the measured target; Hei is the height of the measured target; Wei is the weight of the measured target; Gen is the gender of the measured target; and Z is a pulse wave feature parameter.

With reference to any one of the first aspect to the eighth possible implementation manner of the first aspect, in a ninth possible implementation manner of the first aspect, the activity status of the measured target includes a moving state or a static state, and the activity status of the measured target is determined according to the acceleration signal and/or the angular velocity signal of the measured target;

the measurement location of the pulse wave includes a left limb or a right limb; and the measurement location of the pulse wave is determined according to a feature of a reference point of the electrocardio signal, or is determined according to an acceleration and/or an angular velocity of the measured target, or is determined according to an amplitude of the pulse wave signal of the measured target; and the posture of the measured target includes at least one of a sitting posture, a standing posture, a squatting posture, or a lying posture, and the posture of the measured target is determined according to the acceleration signal and/or the angular velocity signal of the measured target, and/or a feature of the pulse wave signal of the measured target.

According to a second aspect, a blood pressure measurement apparatus is provided, where the blood pressure measurement apparatus includes:

a feature information obtaining unit, configured to obtain first biometric feature information of a measured target, where the first biometric feature information includes a pulse wave signal and/or an electrocardio signal of the measured target;

a status obtaining unit, configured to obtain a first status of the measured target according to the first biometric feature information, where the first status includes at least one of an activity status of the measured target, a posture of the measured target, or a measurement location of a pulse wave of the measured target;

a blood pressure calculation policy determining unit, configured to determine a blood pressure calculation policy of the measured target according to the first status; and a blood pressure value determining unit, configured to determine a blood pressure value of the measured target according to the blood pressure calculation policy and the first biometric feature information.

With reference to the second aspect, in a first possible implementation manner of the second aspect, the first biometric feature information of the measured target further includes:

an acceleration signal and/or an angular velocity signal of the measured target.

With reference to the second aspect or the first possible implementation manner of the second aspect, in a second possible implementation manner of the second aspect, the blood pressure calculation policy determining unit is further configured to: if the blood pressure measurement apparatus is calibrated when the measured target is in the first status, determine that the blood pressure calculation policy of the measured target is a calibrated blood pressure calculation policy; or the blood pressure calculation policy determining unit is further configured to: if the blood pressure measurement apparatus is uncalibrated when the measured target is in the first status, determine that the blood pressure calculation policy of the measured target is an uncalibrated blood pressure calculation policy.

With reference to the second possible implementation manner of the second aspect, in a third possible implementation manner of the second aspect, the blood pressure calculation policy determining unit is further configured to determine a calibrated blood pressure calculation model and a calibration parameter corresponding to the first status in the calibrated blood pressure calculation model.

With reference to the third possible implementation manner of the second aspect, in a fourth possible implementation manner of the second aspect, the blood pressure calculation policy determining unit is further configured to determine a first calibrated blood pressure calculation model according to the first status.

With reference to the third possible implementation manner of the second aspect or the fourth possible implementation manner of the second aspect, in a fifth possible implementation manner of the second aspect, the calibrated blood pressure calculation model is:

$$DBP = \frac{SBP_0}{3} + \frac{2DBP_0}{3} + A\ln\left(\frac{PTT_0}{PTT}\right) - \frac{(SBP_0 - DBP_0)}{3}\frac{PTT^2}{PTT_0^2}$$

$$SBP = DBP + (SBP_0 - DBP_0)\frac{PTT_0^2}{PTT^2},$$

where

SBP is systolic blood pressure; DBP is diastolic blood pressure; PTT is a pulse wave transmission time; A is a blood pressure calculation coefficient; and $SBP_0$, $DBP_0$, and $PTT_0$ are calibration parameters in the calibrated blood pressure calculation model.

With reference to any one of the second aspect to the fifth possible implementation manner of the second aspect, in a sixth possible implementation manner of the second aspect, the blood pressure measurement apparatus further includes a calibrating unit, configured to: before the blood pressure measurement apparatus obtains the first biometric feature information of the measured target, calibrate the blood pressure measurement apparatus, where the calibrating unit is further configured to obtain second biometric feature information of the measured target, where the second biometric feature information includes a pulse wave signal and/or an electrocardio signal of the measured target;

the calibrating unit is further configured to obtain a second status of the measured target according to the second biometric feature information, where the second status includes at least one of an activity status of the measured target, a posture of the measured target, or a measurement location of a pulse wave of the measured target;

the calibrating unit is further configured to obtain a standard blood pressure value when the measured target is in the second status; and the calibrating unit is further configured to determine, according to the standard blood pressure value and the second biometric feature information, a calibration parameter corresponding to the second status in the calibrated blood pressure calculation model.

With reference to the second possible implementation manner of the second aspect, in a seventh possible implementation manner of the second aspect, the blood pressure calculation policy determining unit is further configured to determine an uncalibrated blood pressure calculation model and a body parameter of the measured target, where the body parameter of the measured target includes at least one of age, gender, height, or weight.

With reference to the seventh possible implementation manner of the second aspect, in an eighth possible implementation manner of the second aspect, the uncalibrated blood pressure calculation model is:

$$SBP = A_1 \ln PTT + A_2 Age + A_3 Hei + A_4 Wei + A_5 Gen + A_6 \ln Z + A_7$$

$$DBP = B_1 \ln PTT + B_2 Age + B_3 Hei + B_4 Wei + B_5 Gen + B_6 \ln Z + B_7, \text{ where}$$

SBP is systolic blood pressure; DBP is diastolic blood pressure; $A_1$, $A_2$, $A_3$, $A_4$, $A_5$, $A_6$, and $A_7$ are systolic blood pressure calculation coefficients; $B_1$, $B_2$, $B_3$, $B_4$, $B_5$, $B_6$, and $B_7$ are diastolic blood pressure calculation coefficients; PTT is a pulse wave transmission time; Age is the age of the measured target; Hei is the height of the measured target; Wei is the weight of the measured target; Gen is the gender of the measured target; and Z is a pulse wave feature parameter.

With reference to any one of the second aspect to the eighth possible implementation manner of the second aspect, in a ninth possible implementation manner of the second aspect, the activity status of the measured target includes a moving state or a static state, and the activity status of the measured target is determined by the status obtaining unit according to the acceleration signal and/or the angular velocity signal of the measured target.

the measurement location of the pulse wave includes a left limb or a right limb; and the measurement location of the pulse wave is determined by the status obtaining unit according to a feature of a reference point of the electrocardio signal, or is determined according to an acceleration and/or an angular velocity of the measured target, or is determined according to an amplitude of the pulse wave signal of the measured target; and the posture of the measured target includes at least one of a sitting posture, a standing posture, a squatting posture, or a lying posture, and the posture of the measured target is determined by the status obtaining unit according to the acceleration signal and/or the angular velocity signal of the measured target, and/or a feature of the pulse wave signal of the measured target.

According to a third aspect, a terminal is provided, where the terminal includes a processor, a storage device, and a communications interface, where the storage device is configured to store computer-executable program code;

the processor, the storage device, and the communications interface communicate with each other by using a bus; and the processor reads the program code and data that are stored in the storage device to perform the following operations:

obtaining first biometric feature information of a measured target, where the first biometric feature information includes a pulse wave signal and/or an electrocardio signal of the measured target;

obtaining a first status of the measured target according to the first biometric feature information, where the first status includes at least one of an activity status of the measured target, a posture of the measured target, or a measurement location of a pulse wave of the measured target;

determining a blood pressure calculation policy of the measured target according to the first status; and determining a blood pressure value of the measured target according to the blood pressure calculation policy and the first biometric feature information.

With reference to the third aspect, in a first possible implementation manner of the third aspect, the first biometric feature information of the measured target further includes:

an acceleration signal and/or an angular velocity signal of the measured target.

With reference to the third aspect or the first possible implementation manner of the third aspect, in a second possible implementation manner of the third aspect, the processor is further configured to: if the terminal is calibrated when the measured target is in the first status, determine that the blood pressure calculation policy of the measured target is a calibrated blood pressure calculation policy; or the processor is further configured to: if the terminal is uncalibrated when the measured target is in the first status, determine that the blood pressure calculation policy of the measured target is an uncalibrated blood pressure calculation policy.

With reference to the second possible implementation manner of the third aspect, in a third possible implementation manner of the third aspect, the processor is further configured to determine a calibrated blood pressure calculation model and a calibration parameter corresponding to the first status in the calibrated blood pressure calculation model.

With reference to the third possible implementation manner of the third aspect, in a fourth possible implementation manner of the third aspect, the processor is further configured to determine a first calibrated blood pressure calculation model according to the first status.

With reference to the third possible implementation manner of the third aspect or the fourth possible implementation manner of the third aspect, in a fifth possible implementation manner of the third aspect, the calibrated blood pressure calculation model is:

$$DBP = \frac{SBP_0}{3} + \frac{2DBP_0}{3} + A\ln\left(\frac{PTT_0}{PTT}\right) - \frac{(SBP_0 - DBP_0)}{3}\frac{PTT^2}{PTT_0^2}$$

$$SBP = DBP + (SBP_0 - DBP_0)\frac{PTT_0^2}{PTT^2},$$

where

SBP is systolic blood pressure; DBP is diastolic blood pressure; PTT is a pulse wave transmission time; A is a blood pressure calculation coefficient; and $SBP_0$, $DBP_0$, and $PTT_0$ are calibration parameters in the calibrated blood pressure calculation model.

With reference to any one of the third aspect to the fifth possible implementation manner of the third aspect, in a sixth possible implementation manner of the third aspect, the processor is further configured to: before the blood pressure meter obtains the first biometric feature information of the measured target, calibrate the terminal, where the processor that calibrates the terminal is specifically configured to:

obtain second biometric feature information of the measured target, where the second biometric feature information includes a pulse wave signal and/or an electrocardio signal of the measured target;

obtain a second status of the measured target according to the second biometric feature information, where the second status includes at least one of an activity status of the measured target, a posture of the measured target, or a measurement location of a pulse wave of the measured target;

obtain a standard blood pressure value when the measured target is in the second status; and determine, according to the standard blood pressure value and the second biometric feature information, a calibration parameter corresponding to the second status in the calibrated blood pressure calculation model.

With reference to the second possible implementation manner of the third aspect, in a seventh possible implementation manner of the third aspect, the processor is further configured to determine an uncalibrated blood pressure calculation model and a body parameter of the measured target, where the body parameter of the measured target includes at least one of age, gender, height, or weight.

With reference to the seventh possible implementation manner of the third aspect, in an eighth possible implementation manner of the third aspect, the uncalibrated blood pressure calculation model is:

$SBP=A_1 \ln PTT+A_2Age+A_3Hei+A_4Wei+A_5Gen+A_6 \ln Z+A_7$ $DBP=B_1 \ln PTT+B_2Age+B_3Hei+B_4Wei+B_5Gen+B_6 \ln Z+B_7$, where SBP is systolic blood pressure; DBP is diastolic blood pressure; $A_1$, $A_2$, $A_3$, $A_4$, $A_5$, $A_6$, and $A_7$ are systolic blood pressure calculation coefficients; $B_1$, $B_2$, $B_3$, $B_4$, $B_5$, $B_6$, and $B_7$ are diastolic blood pressure calculation coefficients; PTT is a pulse wave transmission time; Age is the age of the measured target; Hei is the height of the measured target; Wei is the weight of the measured target; Gen is the gender of the measured target; and Z is a pulse wave feature parameter.

With reference to any one of the third aspect to the eighth possible implementation manner of the third aspect, in a ninth possible implementation manner of the third aspect, the activity status of the measured target includes a moving state or a static state, and the processor is further configured to determine the activity status of the measured target according to the acceleration signal and/or the angular velocity signal of the measured target;

the measurement location of the pulse wave includes a left limb or a right limb; and the processor is further configured to determine the measurement location of the pulse wave according to a feature of a reference point of the electrocardio signal, or according to an acceleration and/or an angular velocity of the measured target, or according to an amplitude of the pulse wave signal of the measured target; and the posture of the measured target includes at least one of a sitting posture, a standing posture, a squatting posture, or a lying posture, and the processor is further configured to determine the posture of the measured target according to the acceleration signal and/or the angular velocity signal of the measured target, and/or a feature of the pulse wave signal of the measured target.

The embodiments of the present invention provide a blood pressure measurement method, a blood pressure measurement apparatus, and a terminal. In the method, a blood pressure meter obtains first biometric feature information of a measured target, where the first biometric feature information of the measured target includes a pulse wave signal and/or an electrocardio signal of the measured target; the blood pressure meter obtains a first status of the measured target according to the first biometric feature information of the measured target, determines a blood pressure calculation policy of the measured target according to the first status of the measured target, and determines a blood pressure value of the measured target according to the blood pressure calculation policy and the first biometric feature information of the measured target. By means of the blood pressure measurement method, the blood pressure measurement apparatus, and the terminal in the embodiments of the present invention, impact of a biometric feature and a state of a measured target on blood pressure is considered during blood pressure measurement, and an appropriate blood pressure calculation policy is selected to determine a blood pressure value of the measured target, thereby increasing precision of the blood pressure measurement.

It should be understood that, the above general descriptions and the following detailed descriptions are merely examples, and do not intend to limit the protection scope of the present invention.

BRIEF DESCRIPTION OF DRAWINGS

To describe the technical solutions in the embodiments of the present invention more clearly, the following briefly describes the accompanying drawings required for describing the embodiments or the prior art. Apparently, the accompanying drawings in the following description show merely some embodiments of the present invention, and a person of ordinary skill in the art may still derive other drawings from these accompanying drawings without creative efforts.

FIG. 2(*b*) is a schematic diagram of a signal collected by a three-axis gyroscope which is shown that a measurement location is an inner side of a left arm;

FIG. 2(*c*) is a schematic diagram of a signal collected by a three-axis gyroscope which is shown that a measurement location is an inner side of a left arm;

FIG. 2(*d*) is a schematic diagram of a signal collected by a three-axis gyroscope which is shown that a measurement location is an inner side of a left arm;

FIG. 3(*b*) is a schematic diagram of an electrocardio signal when a blood pressure meter is worn on a left hand according to an embodiment of the present invention;

The foregoing accompanying drawings show specific embodiments of the present invention, and more detailed descriptions are provided in the following. The accompanying drawings and text descriptions are not intended to limit the scope of the idea of the present invention in any manner, but are intended to describe the concept of the present invention to a person skilled in the art with reference to particular embodiments.

DESCRIPTION OF EMBODIMENTS

The following clearly describes the technical solutions in the embodiments of the present invention with reference to the accompanying drawings in the embodiments of the present invention. Apparently, the described embodiments are merely some but not all of the embodiments of the present invention. All other embodiments obtained by a person of ordinary skill in the art based on the embodiments of the present invention without creative efforts shall fall within the protection scope of the present invention.

Numerous specific details are mentioned in the following detailed descriptions to provide a thorough understanding of the present invention. However, a person skilled in the art should understand that the present invention may be implemented without these specific details. In other embodiments, a method, a process, a component, and a circuit that are publicly known are not described in detail so as not to unnecessarily obscure the embodiments.

In the embodiments of the present invention, it should be understood that ordinal numbers such as "first" and "second" are used only for differentiation unless they actually indicate a sequence with reference to the context.

The embodiments of the present invention provide a blood pressure measurement method, a blood pressure measurement apparatus, and a terminal, so as to increase precision of blood pressure detection.

Figure 1:
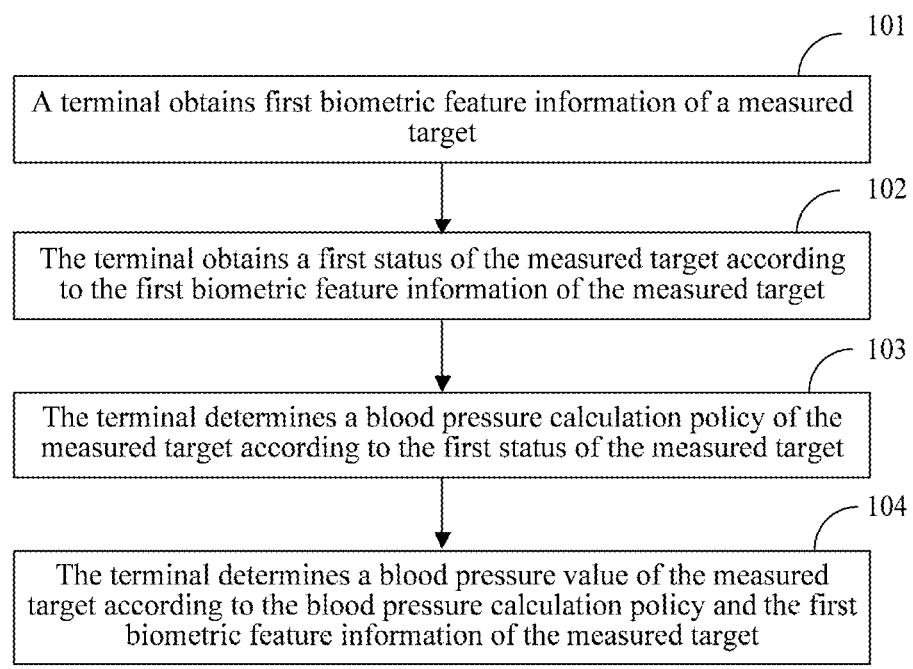
FIG. 1 is a flowchart of a blood pressure measurement method according to an embodiment of the present invention.

FIG. 1 is a flowchart of a blood pressure measurement method according to an embodiment of the present invention. The blood pressure measurement method in this embodiment of the present invention is implemented by a terminal. The terminal may be, for example, a wearable device having a blood pressure measurement function, such as a cuff-less blood pressure meter. The following provides description by using an example in which a blood pressure meter is used as the terminal in this embodiment.

As shown in FIG. 1, the method includes the following steps.

Step 101: The blood pressure meter obtains first biometric feature information of a measured target.

In this embodiment of the present invention, the first biometric feature information of the measured target includes a pulse wave signal and/or an electrocardio signal of the measured target.

Further, in this embodiment of the present invention, the first biometric feature information of the measured target further includes an acceleration signal and/or an angular velocity signal of the measured target.

In this embodiment of the present invention, pulse wave signals may be collected by using an optical sensor, a pressure sensor, an acoustic sensor, a photoelectric sensor, an acceleration sensor, or displacement sensor. Electrocardio signals may be collected by using an electrocardio sensor. Acceleration signals and/or angular velocity signals may be collected by using an acceleration sensor, a gyroscope, a magnetometer, or the like. For a specific collection method, details are not described herein.

In this embodiment of the present invention, filtering processing may be performed on the collected electrocardio signals and/or pulse wave signals. Performing filtering processing on the electrocardio signal and/or the pulse wave signal is to filter out interference, and any filtering method in the prior art may be used. Details are not described herein.

Step 102: The blood pressure meter obtains a first status of the measured target according to the first biometric feature information of the measured target.

In this embodiment of the present invention, the first status of the measured target includes at least one of an activity status of the measured target, a posture of the measured target, or a measurement location of a pulse wave of the measured target.

The activity status of the measured target includes a moving state or a static state, and the activity status of the measured target is determined according to the acceleration signal and/or the angular velocity signal of the measured target.

The posture of the measured target includes at least one of a sitting posture, a standing posture, a squatting posture, or a lying posture, and the posture of the measured target is determined according to the acceleration signal and/or the angular velocity signal of the measured target, and/or a feature of the pulse wave signal of the measured target.

The measurement location of the pulse wave includes a left limb or a right limb, and the measurement location further includes an upper limb or a lower limb, or an outer side of a limb or an inner side of a limb. The measurement location of the pulse wave is determined according to a feature of a reference point of the electrocardio signal, or the measurement location of the pulse wave is determined according to an acceleration and/or an angular velocity of the measured target, or the measurement location of the pulse wave is determined according to an amplitude of the pulse wave signal of the measured target.

For example, it is determined, according to an amplitude of a pulse wave signal, that a location on which the blood pressure meter measures a pulse wave is on an outer side of a limb or an inner side of a limb. Because a radial artery is near an inner side of an arm, an amplitude of a pulse wave signal on an inner side of a limb is greater than an amplitude of a pulse wave signal on an outer side of the limb.

Specifically, the measurement location of the pulse wave may be detected by using a three-axis gyroscope. FIG. 2 is a schematic diagram of a signal collected by a three-axis gyroscope according to an embodiment of the present invention. As shown in FIG. 2, a measurement location of a pulse wave of a user may be determined according to signal components on an X axis, a Y axis, and a Z axis.

Figure 2A:
FIG. 2(*a*) is a schematic diagram of a signal collected by a three-axis gyroscope which is shown that a measurement location is an inner side of a left arm.

As shown in FIG. 2(a), an amplitude of a signal on an X axis is greater than amplitudes of signals on a Y axis and a Z axis; the amplitude of the signal on the Y axis fluctuates from positive to negative; and the amplitude of the signal on the Z axis fluctuates from negative to positive. A measurement location shown in this figure is an inner side of a left arm.

Figure 2B:
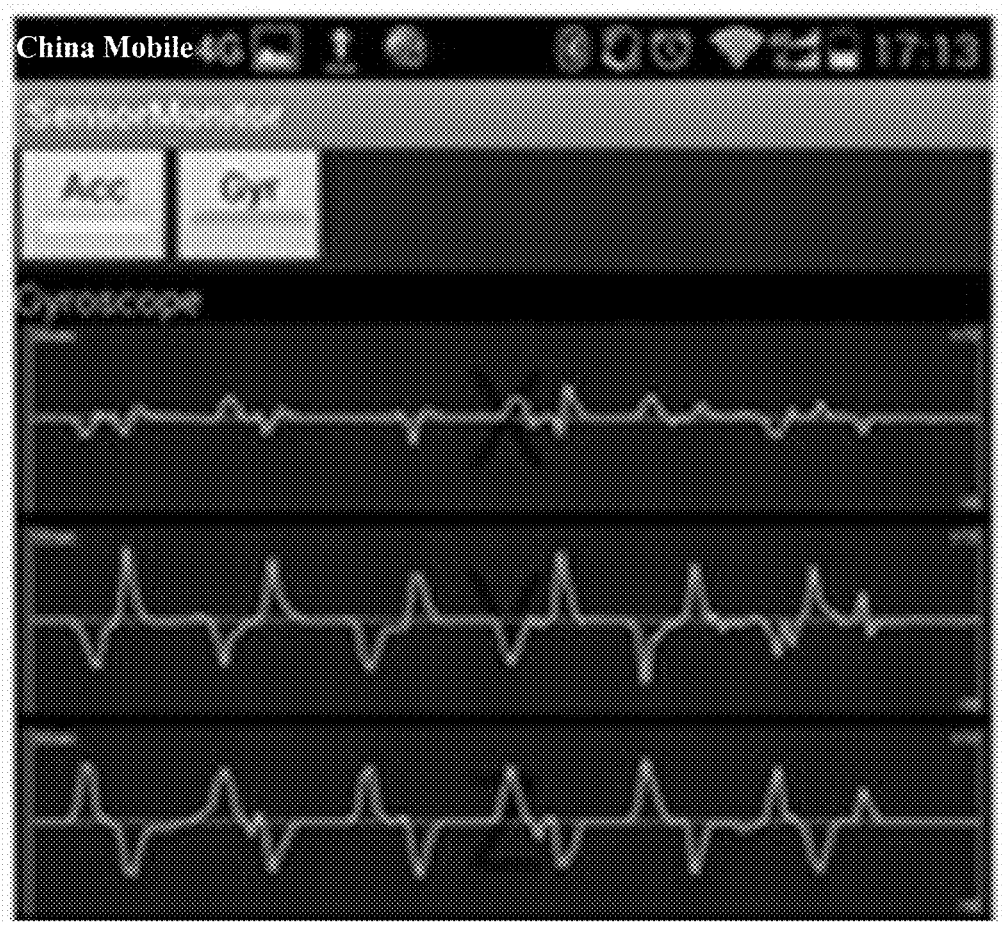

As shown in FIG. 2(b), an amplitude of a signal on an X axis is less than amplitudes of signals on a Y axis and a Z axis; the amplitude of the signal on the Y axis fluctuates from negative to positive; and the amplitude of the signal on the Z axis fluctuates from positive to negative. A measurement location shown in this figure is an outer side of a left arm.

Figure 2C:
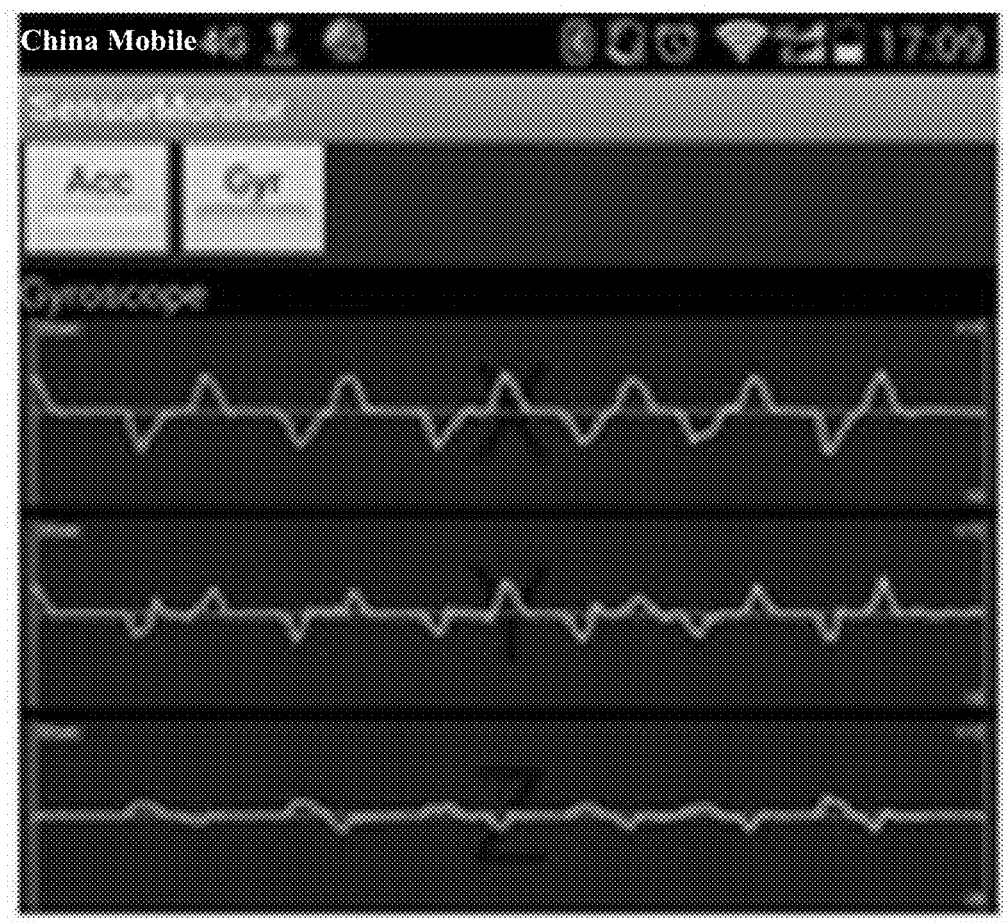

As shown in FIG. 2(c), an amplitude of a signal on an X axis fluctuates obviously; an amplitude of a signal on a Y axis fluctuates from negative to positive; and an amplitude of a signal on a Z axis fluctuates from positive to negative. A measurement location shown in this figure is an inner side of a right arm.

Figure 2D:
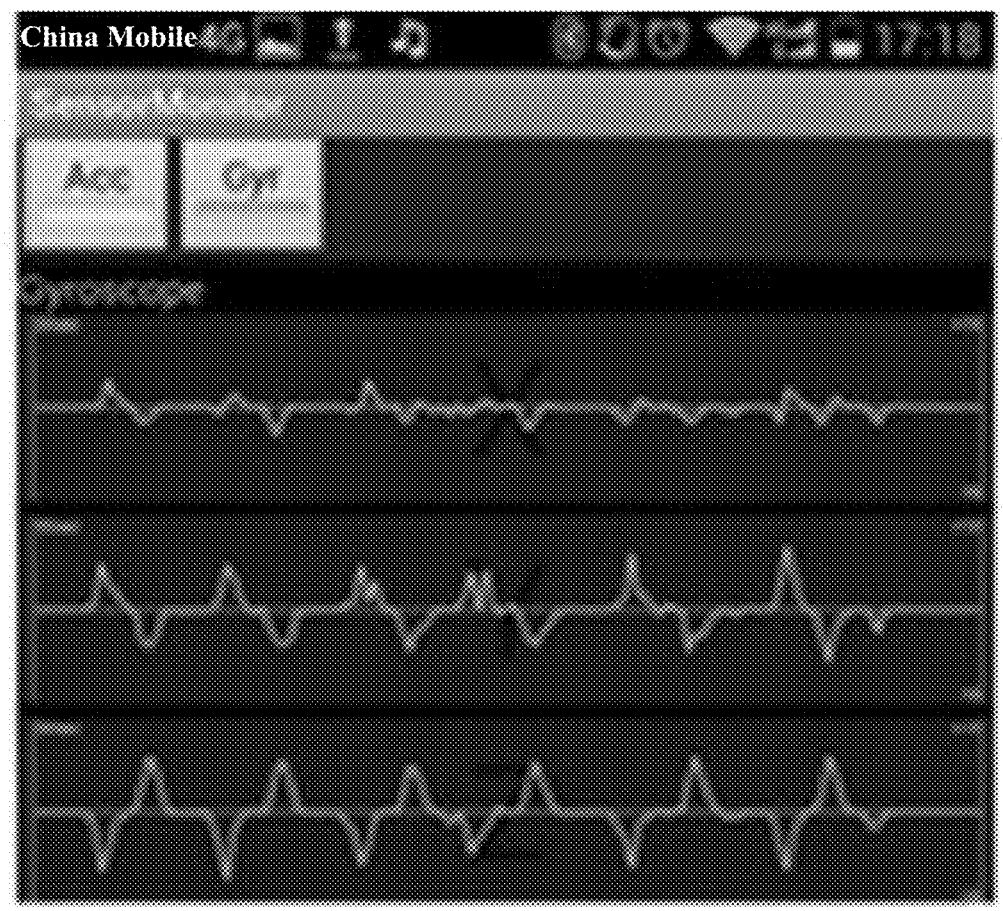

As shown in FIG. 2(d), an amplitude of a signal on an X axis is less than amplitudes of signals on a Y axis and a Z axis; the amplitude of the signal on the Y axis fluctuates from positive to negative; and the amplitude of the signal on the Z axis fluctuates from negative to positive. A measurement location shown in this figure is an outer side of a right arm.

A measurement location of a pulse maybe alternatively detected by using a three-axis accelerometer, which is similar to the three-axis accelerometer, that is, a measurement location of a pulse wave of a user may be determined according to signal components on an X axis, a Y axis, and a Z axis of the three-axis accelerometer. In practice, the determining may be made by using both a three-axis accelerometer and a three-axis gyroscope, which can increase identification accuracy.

A measurement location of a pulse wave may be alternatively determined by using a feature of an electrocardio signal. The electrocardio signal actually refers to a potential difference of different locations on a body surface. For example, when a blood pressure meter is worn on a left arm, the electrocardio signal is a potential value of a right arm minus a potential value of the left arm; or when a blood pressure meter is worn on a right arm, the electrocardio signal is a potential value of a left arm minus a potential value of the right arm. Therefore, when the blood pressure meter worn on different sides, signal features are obviously different.

Figure 3A:
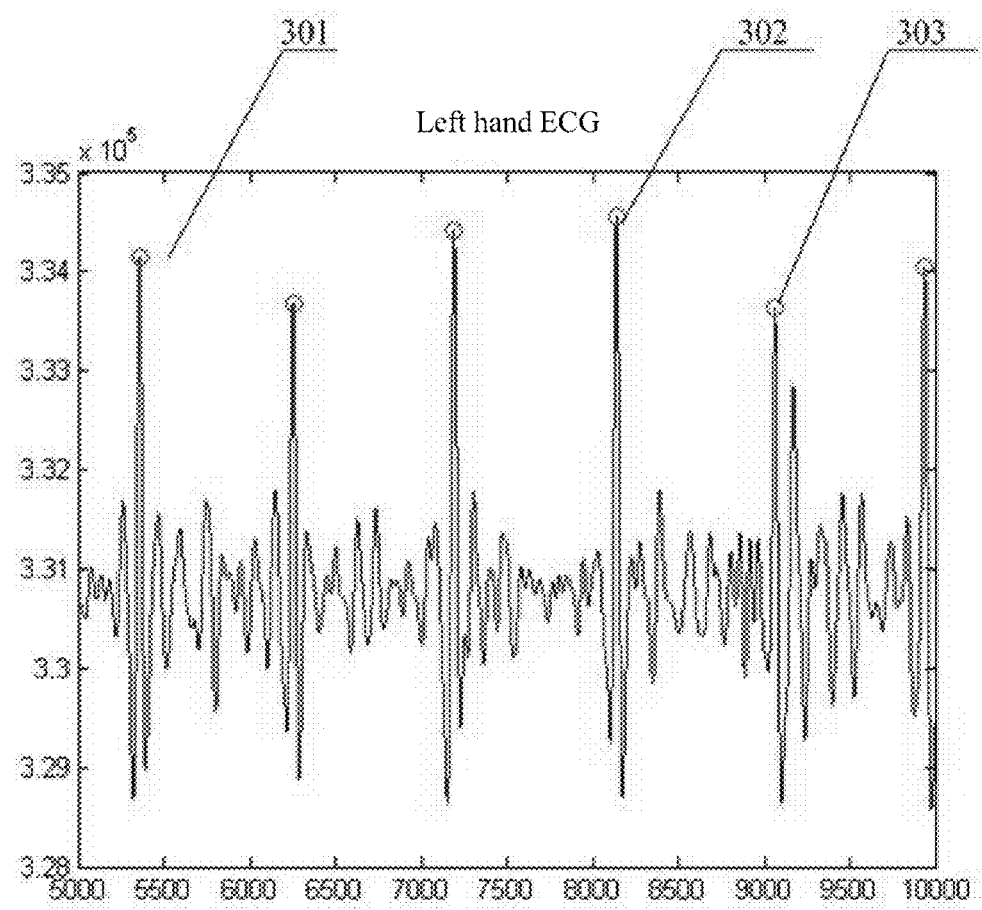
FIG. 3(*a*) is a schematic diagram of an electrocardio signal when a blood pressure meter is worn on a left hand according to an embodiment of the present invention.

FIG. 3 is a schematic diagram of an electrocardio signal according to an embodiment of the present invention. As shown in FIG. 3(a), when a blood pressure meter is worn on a left hand, vertexes 301, 302, and 303 of an R wave of an electrocardio signal are above a baseline. FIG. 3(a) merely shows a part of the R wave and vertexes of the R wave as an example.

Figure 3B:
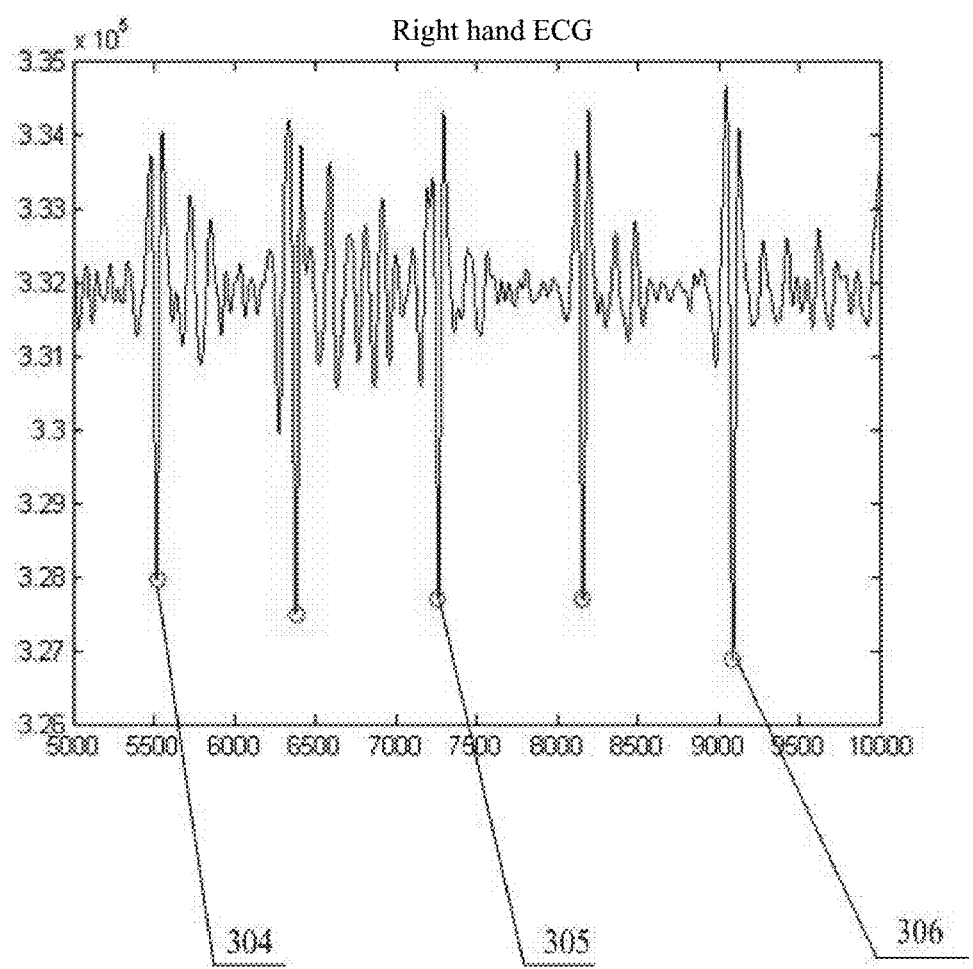

When the blood pressure meter is worn on a right hand, vertexes 304, 305, and 306 of an R wave of an electrocardio signal are below the baseline. FIG. 3(b) merely shows a part of the R wave and vertexes of the R wave as an example.

In another embodiment of the present invention, it may be alternatively defined that when a blood pressure meter is worn on a right arm, an electrocardio signal is a potential value of a left arm minus a potential value of the right arm; or when a blood pressure meter is worn on a left arm, an electrocardio signal is a potential value of a right arm minus a potential value of the left arm. A definition manner of a blood pressure meter is preset at delivery.

In an actual application, a case in which it is difficult to determine whether an R wave of an electrocardio signal is above a baseline or below the baseline may exist. In this case, a determining method using the foregoing gyroscope and/or the accelerometer may be further used for assistance in the determining.

Besides the foregoing method for automatically identifying a measurement location of a pulse wave by using a sensor, in practice, a case in which a user needs to confirm a measurement location of a pulse wave and a location on which a blood pressure meter is worn may also exist. For example, when a user sits and keeps arms flat, and wears a blood pressure meter on one arm, it is difficult to determine, by using a gyroscope and/or an accelerometer, that the blood pressure meter is worn on which arm, and above-mentioned features of an electrocardio signal may also unobvious. In cases in which it is difficult to determine a location on which a blood pressure meter is worn, a user may confirm the location of the blood pressure meter by selecting a screen prompt option, such as a left hand or a right hand, of the blood pressure meter; or by means of voice interaction, where the left hand and the right hand respectively indicate a left arm and a right arm.

In an actual application, a blood pressure meter may alternatively directly determine a measurement location of a pulse wave according to a manner selected by a user instead of determining the measurement location of the pulse wave by using a sensor.

Step 103: The blood pressure meter determines a blood pressure calculation policy of the measured target according to the first status of the measured target.

There are multiple blood pressure calculation policies. For example, a policy of calculating a blood pressure of a left hand or a policy of calculating a blood pressure of a right hand; a policy of calculating a blood pressure when a person is sitting or a policy of calculating a blood pressure when a person is lying; and a policy of calculating a blood pressure when a person is moving or a policy of calculating a blood pressure when a person is static. For another example, a policy of calculating a blood pressure of an inner side of the left hand when a person is sitting, and policy of calculating a blood pressure of an outer side of the right hand when a person is running.

Figure 4:
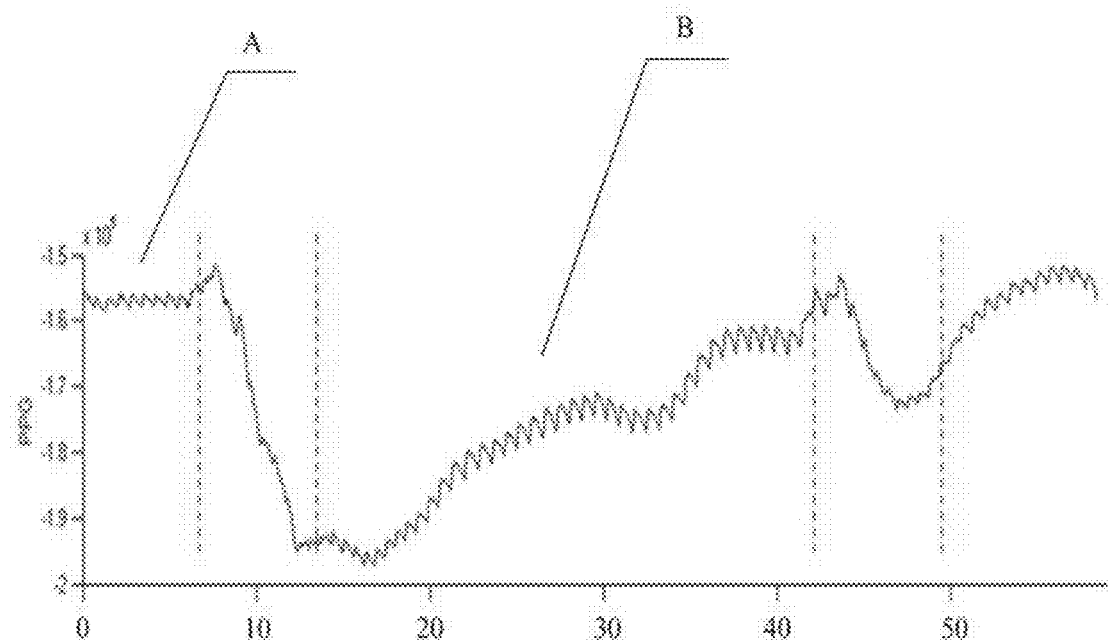
FIG. 4 is a schematic diagram of a change of a pulse wave according to an embodiment of the present invention.

FIG. 4 is a schematic diagram of a change of a pulse wave according to an embodiment of the present invention. As shown in FIG. 4, a pulse wave in an A zone is relatively stable and has a relatively high amplitude, indicating that in this period, a measured user is sitting; and an amplitude of a pulse wave in a B zone changes from high to low and an average amplitude is relatively low, indicating that in this period, the measured user is lying.

It can be seen that a value of blood pressure varies with different first statuses of the measured target. Therefore, this embodiment of the present invention proposes that the blood pressure calculation policy is determined according to the first status of the measured target.

Further, in this embodiment of the present invention, the determining a blood pressure calculation policy specifically includes:

determining a blood pressure calculation model and a body parameter of the measured target, where the body parameter of the measured target includes at least one of age, gender, height, or weight, and in this embodiment of the present invention, for example, the blood pressure calculation model may be:

$$SBP = A_1 \ln PTT + A_2 Age + A_3 Hei + A_4 Wei + A_5 Gen + A_6 \ln Z + A_7 \quad (1)$$

$$DBP = B_1 \ln PTT + B_2 Age + B_3 Hei + B_4 Wei + B_5 Gen + B_6 \ln Z + B_7 \quad (2), \text{where}$$

SBP is systolic blood pressure; DBP is diastolic blood pressure; $A_1$, $A_2$, $A_3$, $A_4$, $A_5$, $A_6$, and $A_7$ are systolic blood pressure calculation coefficients; $B_1$, $B_2$, $B_3$, $B_4$, $B_5$, $B_6$, and $B_7$ are diastolic blood pressure calculation coefficients; PTT is a pulse wave transmission time; Age is the age of the measured target; Hei is the height of the measured target; Wei is the weight of the measured target; Gen is the gender of the measured target; and Z is a pulse wave feature parameter.

The pulse wave feature parameter Z may include at least one of a zero point of a second derivative of the pulse wave, an area of the pulse wave, duration in which the pulse wave goes up, duration in which the pulse wave goes down, or a height of the pulse wave.

In this embodiment of the present invention, due to different first statuses, different values may be selected for one or more of coefficients in the foregoing blood pressure meter. A specific value selecting manner may be determined by analyzing a large amount of experimental data. Coefficients $A_1$ to $A_7$ and $B_1$ to $B_7$ applicable to perform measurement on the measured target in different first statuses are selected, so as to obtain a relatively accurate blood pressure measurement value.

For example, when the first status is a lying posture, coefficients $A_1$ to $A_7$ and $B_1$ to $B_7$ for measuring a blood pressure corresponding to the lying posture are selected. For another example, when the first status is performing measurement on the left side of the body when the measured target is sifting, corresponding coefficients $A_1$ to $A_7$ and $B_1$ to $B_7$ are selected. Therefore, a calculation model may be adjusted by selecting, according to different first statuses, different coefficients of the model.

In this embodiment of the present invention, for example, $A_1$ and $B_1$ may be related to the first status indicating the measurement location of the pulse wave of the measured target, such as a left side of the body or a right side of the body; because a blood pressure value of the left side of the body is usually lower than a blood pressure value of the right side of the body, when it is determined that the first status is the left side of the body, relatively small $A_1$ and $B_1$ are selected; or when it is determined that the first status is the right side of the body, $A_1$ and $B_1$ are relatively greater than $A_1$ and $B_1$ when the first status is the left side of the body. In this case, other coefficients may be constants determined by analyzing experimental data, or may be variables selected according to the measurement location of the pulse wave of the measured target. For another example, $A_7$ and $B_7$ may be related to the first status indicating a posture; because a blood pressure value when a person is lying is greater than a blood pressure value when the person is sifting, when it is determined that the first status is a sitting posture, relatively small $A_7$ and $B_7$ are selected; or when it is determined that the first status is a lying posture, $A_7$ and $B_7$ are relatively greater than $A_7$ and $B_7$ when the first status is a sifting posture. In this case, other coefficients may be constants determined by analyzing experimental data, or may be variables selected according to the posture.

Certainly, the description is merely provided in the foregoing embodiment as an example. In this embodiment of the present invention, coefficients $A_1$ to $A_7$ and $B_1$ to $B_7$ are not specifically limited to be related to which state, and may be specifically analyzed and determined according to experimental data. Determining a blood pressure value of the measured target by selecting different $A_1$ to $A_7$ and $B_1$ to $B_7$ coefficients according to different states belongs to the protection scope of this embodiment of the present invention.

Step 104: The blood pressure meter determines a blood pressure value of the measured target according to the blood pressure calculation policy and the first biometric feature information of the measured target.

In this embodiment of the present invention, the blood pressure meter selects coefficients A1 to A7 and B1 to B7 in a preset blood pressure calculation model according to the first biometric feature information of the measured target, so as to determine a blood pressure value of the measured target by using the foregoing blood pressure calculation model.

The coefficients A1 to A7 and B1 to B7 in the preset blood pressure calculation model are data obtained through a large number of experiments, and may be, for example, stored in a storage unit of the blood pressure meter in a manner of a corresponding table.

The blood pressure meter in this embodiment of the present invention is a cuff-less blood pressure meter, and the blood pressure measurement method in this embodiment of the present invention is implemented by using the cuff-less blood pressure meter. The blood pressure meter obtains first feature information of a measured target, where the first feature information of the measured target includes first biometric feature information; obtains a first status of the measured target according to the first biometric feature information of the measured target; obtains a corresponding blood pressure calculation policy according to the first status of the measured target; and obtains a blood pressure value of the measured target according to the blood pressure calculation policy and the measured target. By means of the blood pressure measurement method and the blood pressure meter in the embodiments of the present invention, during blood pressure measurement, a biometric feature and a status of a measured target when the blood pressure measurement is performed on the measured target are considered to determine a blood pressure calculation policy, so that precision is high.

Figure 5:
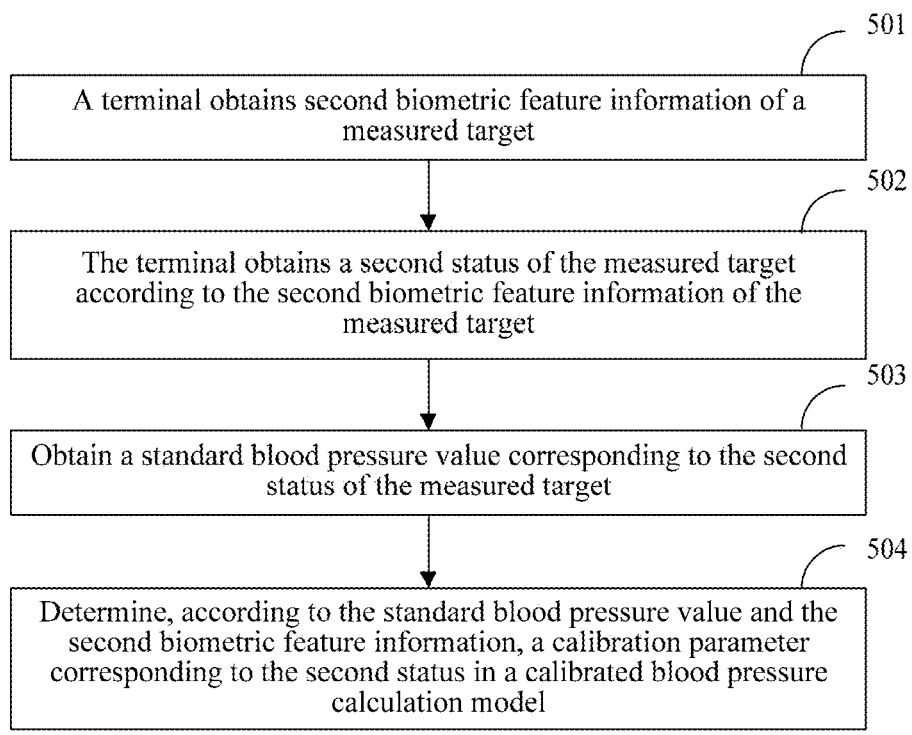
FIG. 5 is a flowchart of a method for calibrating a blood pressure meter according to an embodiment of the present invention.

Further, in this embodiment of the present invention, before the obtaining first biometric feature information of a measured target, the method may further include calibrating the blood pressure meter. FIG. 5 is a flowchart of a method for calibrating a blood pressure meter according to an embodiment of the present invention. As shown in FIG. 5, the method for calibrating a blood pressure meter includes the following steps.

Step 501: The blood pressure meter obtains second biometric feature information of a measured target.

The second biometric feature information of the measured target includes a pulse wave signal and/or an electrocardio signal of the measured target.

Step 502: The blood pressure meter obtains a second status of the measured target according to the second biometric feature information of the measured target.

The second status of the measured target includes at least one of an activity status of the measured target, a posture of the measured target, or a measurement location of a pulse wave of the measured target.

Step 503: Obtain a standard blood pressure value corresponding to the second status of the measured target.

Step 504: Determine, according to the standard blood pressure value and the second biometric feature information, a calibration parameter corresponding to the second status in a calibrated blood pressure calculation model.

In this embodiment of the present invention, a blood pressure meter may be calibrated when the blood pressure meter is used for the first time or when an unrecorded measured target is changed. Once a blood pressure meter is calibrated when a measured target is in a state, the blood pressure meter does not need to be calibrated again when the measured target is in the same state, and the blood pressure meter automatically invokes stored data, thereby simplifying operation steps. In addition, by calibrating a blood pressure meter when a measured user is in different states, precision of blood pressure measurement is increased.

The calibrated blood pressure calculation model may be a model unrelated to the state of the measured target, or may be multiple models corresponding to different states. A specific method for obtaining the calibrated blood pressure calculation model and a calibration parameter thereof is the same as that for step 501 to step 504, and details are not described herein again.

Certainly, the blood pressure meter may alternatively directly perform blood pressure measurement on the measured target without being calibrated.

Further, in step 103 in this embodiment of the present invention, the determining, by the blood pressure meter, a blood pressure calculation policy of the measured target according to the first status of the measured target may specifically include:

if the blood pressure meter is calibrated when the measured target is in the first status, determining that the blood pressure calculation policy of the measured target is a calibrated blood pressure calculation policy; or if the blood pressure meter is uncalibrated when the measured target is in the first status, determining that the blood pressure calculation policy of the measured target is an uncalibrated blood pressure calculation policy.

If the blood pressure meter is calibrated when the measured target is in the first status, there may be one or more calibrated blood pressure calculation models. When the calibrated blood pressure calculation model is a model unrelated to the state of the measured target, that is, the blood pressure calculation model is related to only the blood pressure meter, the determining that the blood pressure calculation policy of the measured target is a calibrated blood pressure calculation policy specifically includes:

determining a calibrated blood pressure calculation model and a calibration parameter corresponding to the first status in the calibrated blood pressure calculation model.

Optionally, when the calibrated blood pressure calculation model is multiple models corresponding to multiple states, the determining that the blood pressure calculation policy of the measured target is a calibrated blood pressure calculation policy specifically includes:

determining a calibrated blood pressure calculation model corresponding to the first status and a calibration parameter corresponding to the first status in the calibrated blood pressure calculation model.

In this embodiment of the present invention, the calibrated blood pressure calculation model may be, for example, $$DBP = \frac{SBP_0}{3} + \frac{2DBP_0}{3} + A\ln\left(\frac{PTT_0}{PTT}\right) - \frac{(SBP_0 - DBP_0)}{3}\frac{PTT^2}{PTT_0^2} \quad (3)$$

$$SBP = DBP + (SBP_0 - DBP_0)\frac{PTT_0^2}{PTT^2}, \quad (4)$$

where

SBP is systolic blood pressure; DBP is diastolic blood pressure; PTT is a pulse wave transmission time; A is a blood pressure calculation coefficient; and $SBP_0$, $DBP_0$, and $PTT_0$ are calibration parameters in the calibrated blood pressure calculation model.

In an actual application, the calibration parameter in the calibrated calculation model includes $SBP_0$, $DBP_0$, and $PTT_0$, where $SBP_0$ and $DBP_0$ are entered by a user in a corresponding state after blood pressure measurement is performed on the user by using a cuff blood pressure meter; and $PTT_0$ is a value calculated by using pulse wave data and electrocardio data of the used user in the corresponding state.

If the blood pressure meter is uncalibrated when the measured target is in the first status, in this embodiment of the present invention, the determining that the blood pressure calculation policy of the measured target is an uncalibrated blood pressure calculation policy specifically includes:

obtaining an uncalibrated blood pressure calculation model and a body parameter of the measured target, where the body parameter of the measured target includes at least one of age, gender, height, or weight.

In this embodiment of the present invention, if the blood pressure meter is uncalibrated when the measured target is in the first status, the determining the blood pressure calculation policy is specifically the same as the obtaining, by the blood pressure meter, blood pressure calculation policy according to the first status of the measured target in step 103, and the same blood pressure calculation model may be used to obtain a blood pressure value of the measured target, and details are not described herein again.

Further, if the blood pressure meter is uncalibrated when the measured target is in the first status, the blood pressure meter may prompt the user to go to a calibrating process. If the user does not select the calibrating process to calibrate the blood pressure meter, the blood pressure meter performs blood pressure measurement according to the forgoing method in which the blood pressure meter is uncalibrated.

Figure 6:
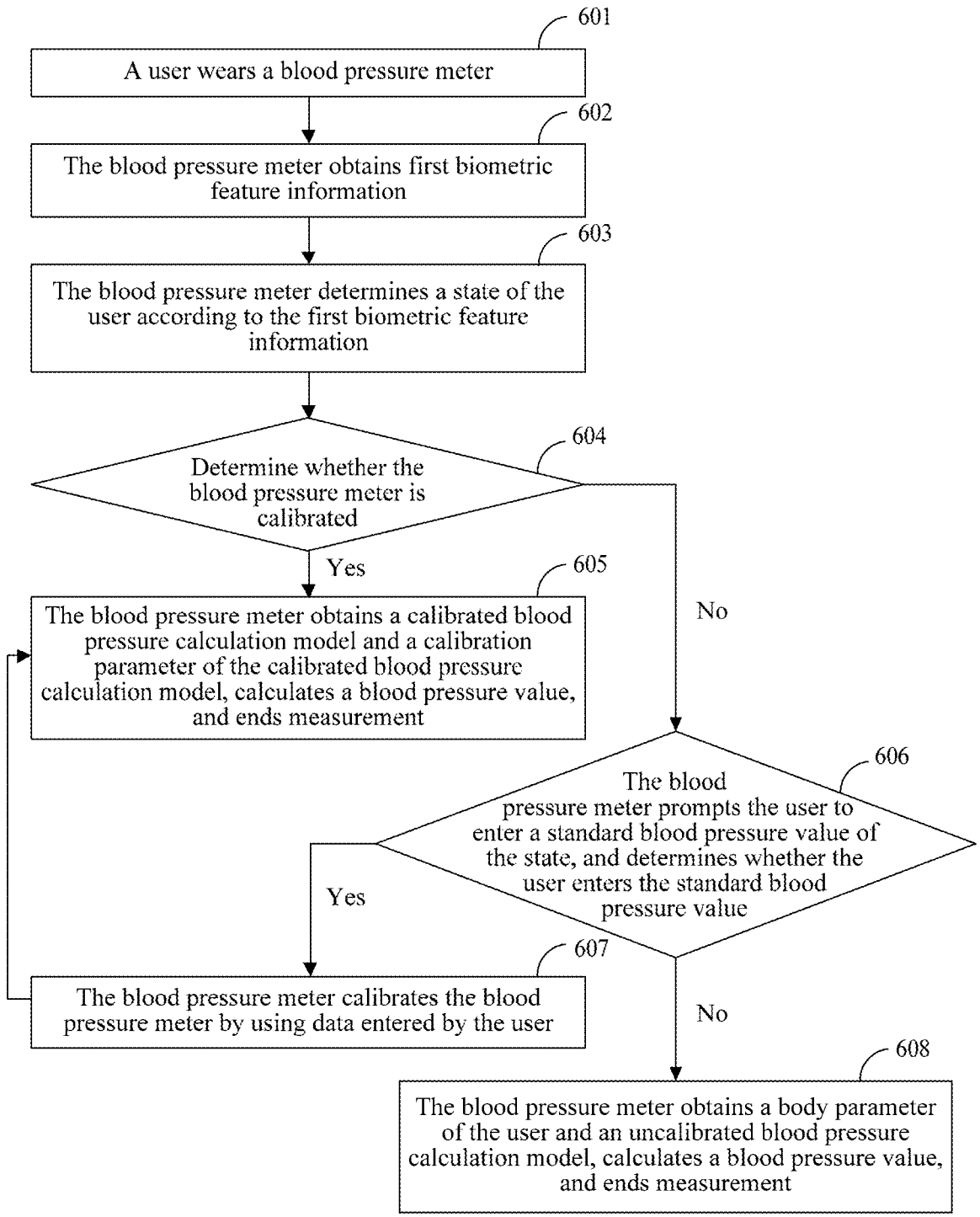
FIG. 6 is a flowchart of a blood pressure measurement method according to an embodiment of the present invention.

FIG. 6 is a flowchart of a blood pressure measurement method according to an embodiment of the present invention. As shown in FIG. 6, the method includes the following steps.

Step 601: A user wears a blood pressure meter.

Step 602: The blood pressure meter obtains first biometric feature information, such as a pulse wave signal, an electrocardio signal, and an acceleration signal and/or the angular velocity signal, of the user.

Step 603: The blood pressure meter determines a state of the user according to the first biometric feature information.

For example, it is determined that the state of the user is in a sitting posture, and the blood pressure meter is worn on an inner side of the right arm.

Step 604: Determine whether the blood pressure meter is calibrated, and if the blood pressure meter is calibrated, go to step 605; or if the blood pressure meter is uncalibrated, go to step 606.

Step 605: The blood pressure meter obtains a calibrated blood pressure calculation model and a calibration parameter of the calibrated blood pressure calculation model, calculates a blood pressure value, and ends measurement.

Step 606: The blood pressure meter prompts the user to enter a standard blood pressure value of the state, and determines whether the user enters the standard blood pressure value, and if yes, go to step 607; or if not, go to step 608.

Step 607: The blood pressure meter calibrates the blood pressure meter by using data entered by the user, and go to step 605.

Step 608: The blood pressure meter obtains a body parameter of the user and an uncalibrated blood pressure calculation model, calculates a blood pressure value, and ends measurement.

The body parameter of a measured target includes at least one of age, gender, height, or weight, which may be entered by the user according to a prompt.

The blood pressure measurement method according to this embodiment of the present invention is easily operated and has high precision.

Corresponding to the foregoing blood pressure measurement method, an embodiment of the present invention further provides a blood pressure meter.

Figure 7:
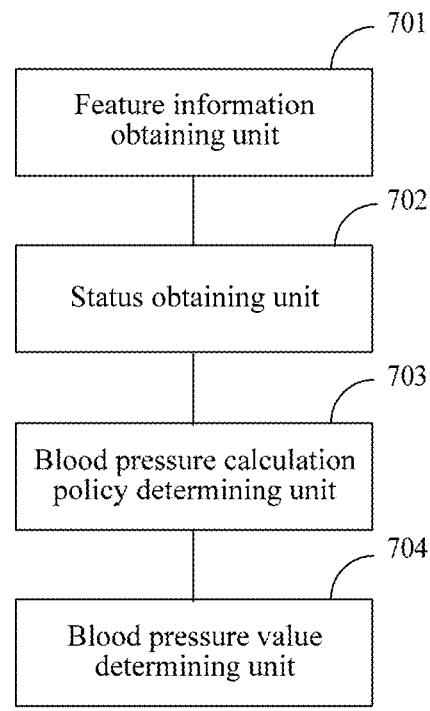
FIG. 7 is a schematic structural diagram of a blood pressure meter according to an embodiment of the present invention.

FIG. 7 is a schematic structural diagram of a blood pressure measurement apparatus according to an embodiment of the present invention, as shown in FIG. 7. The blood pressure measurement apparatus includes:

a feature information obtaining unit 701, configured to obtain first biometric feature information of a measured target, where the first biometric feature information includes a pulse wave signal and/or an electrocardio signal of the measured target;

a status obtaining unit 702, configured to obtain a first status of the measured target according to the first biometric feature information, where the first status includes at least one of an activity status of the measured target, a posture of the measured target, or a measurement location of a pulse wave of the measured target;

a blood pressure calculation policy determining unit 703, configured to determine a blood pressure calculation policy of the measured target according to the first status; and a blood pressure value determining unit 704, configured to determine a blood pressure value of the measured target according to the blood pressure calculation policy and the first biometric feature information.

The blood pressure measurement apparatus according to this embodiment of the present invention obtains first biometric feature information of a measured target; obtains a first status of the measured target according to the first biometric feature information of the measured target; determines a blood pressure calculation policy of the measured target according to the first status of the measured target; and determines a blood pressure value of the measured target according to the blood pressure calculation policy and the first biometric feature information of the measured target. Therefore, the blood pressure measurement apparatus according to this embodiment of the present invention considers impact of a state of a user on a blood pressure during blood pressure measurement and makes an improvement in this respect, thereby increasing measurement precision for the blood pressure measurement apparatus.

Further, in this embodiment of the present invention, the first biometric feature information of the measured target further includes:

an acceleration signal and/or an angular velocity signal of the measured target.

In this embodiment of the present invention, the blood pressure calculation policy determining unit 703 is further configured to: if the blood pressure measurement apparatus is calibrated when the measured target is in the first status, determine that the blood pressure calculation policy of the measured target is a calibrated blood pressure calculation policy; or the blood pressure calculation policy determining unit 703 is further configured to: if the blood pressure measurement apparatus is uncalibrated when the measured target is in the first status, determine that the blood pressure calculation policy of the measured target is an uncalibrated blood pressure calculation policy.

In this embodiment of the present invention, the blood pressure calculation policy determining unit 703 is further configured to determine a calibrated blood pressure calculation model and a calibration parameter corresponding to the first status in the calibrated blood pressure calculation model.

In this embodiment of the present invention, the blood pressure calculation policy determining unit 703 is further configured to determine a first calibrated blood pressure calculation model according to the first status.

The calibrated blood pressure calculation model is:

$$DBP = \frac{SBP_0}{3} + \frac{2DBP_0}{3} + A\ln\left(\frac{PTT_0}{PTT}\right) - \frac{(SBP_0 - DBP_0)}{3} \frac{PTT^2}{PTT_0^2} \quad (3)$$

$$SBP = DBP + (SBP_0 - DBP_0)\frac{PTT_0^2}{PTT^2}, \quad (4)$$

where

SBP is systolic blood pressure; DBP is diastolic blood pressure; PTT is a pulse wave transmission time; A is a blood pressure calculation coefficient; and $SBP_0$, $DBP_0$, and $PTT_0$ are calibration parameters in the calibrated blood pressure calculation model.

In this embodiment of the present invention, the blood pressure measurement apparatus further includes a calibrating unit, configured to: before the blood pressure measurement apparatus obtains the first biometric feature information of the measured target, calibrate the blood pressure measurement apparatus, where the calibrating unit is further configured to obtain second biometric feature information of the measured target, where the second biometric feature information includes a pulse wave signal and/or an electrocardio signal of the measured target;

the calibrating unit is further configured to obtain a second status of the measured target according to the second biometric feature information, where the second status includes at least one of an activity status of the measured target, a posture of the measured target, or a measurement location of a pulse wave of the measured target;

the calibrating unit is further configured to obtain a standard blood pressure value when the measured target is in the second status; and the calibrating unit is further configured to determine, according to the standard blood pressure value and the second biometric feature information, a calibration parameter corresponding to the second status in the calibrated blood pressure calculation model.

In this embodiment of the present invention, the blood pressure calculation policy determining unit 703 is further configured to determine an uncalibrated blood pressure calculation model and a body parameter of the measured target, where the body parameter of the measured target includes at least one of age, gender, height, or weight.

In this embodiment of the present invention, the uncalibrated blood pressure calculation model is:

$$SBP = A_1 \ln PTT + A_2 Age + A_3 Hei + A_4 Wei + A_5 Gen + A_6 \ln Z + A_7 \quad (1)$$

$$DBP = B_1 \ln PTT + B_2 Age + B_3 Hei + B_4 Wei + B_5 Gen + B_6 \ln Z + B_7 \quad (2),$$ where SBP is systolic blood pressure; DBP is diastolic blood pressure; $A_1$, $A_2$, $A_3$, $A_4$, $A_5$, $A_6$, and $A_7$ are systolic blood pressure calculation coefficients; $B_1$, $B_2$, $B_3$, $B_4$, $B_5$, $B_6$, and $B_7$ are diastolic blood pressure calculation coefficients; PTT is a pulse wave transmission time; Age is the age of the measured target; Hei is the height of the measured target; Wei is the weight of the measured target; Gen is the gender of the measured target; and Z is a pulse wave feature parameter.

In this embodiment of the present invention, the activity status of the measured target includes a moving state or a static state, and the activity status of the measured target is determined by the status obtaining unit 702 according to the acceleration signal and/or the angular velocity signal of the measured target;

the measurement location of the pulse wave includes a left limb or a right limb; and the measurement location of the pulse wave is determined by the status obtaining unit 702 according to a feature of a reference point of the electrocardio signal, or is determined according to an acceleration and/or an angular velocity of the measured target, or is determined according to an amplitude of the pulse wave signal of the measured target; and the posture of the measured target includes at least one of a sitting posture, a standing posture, a squatting posture, or a lying posture, and the posture of the measured target is determined by the status obtaining unit 702 according to the acceleration signal and/or the angular velocity signal of the measured target, and/or a feature of the pulse wave signal of the measured target.

The blood pressure meter according to this embodiment of the present invention can increase precision of high blood pressure measurement.

Figure 8:
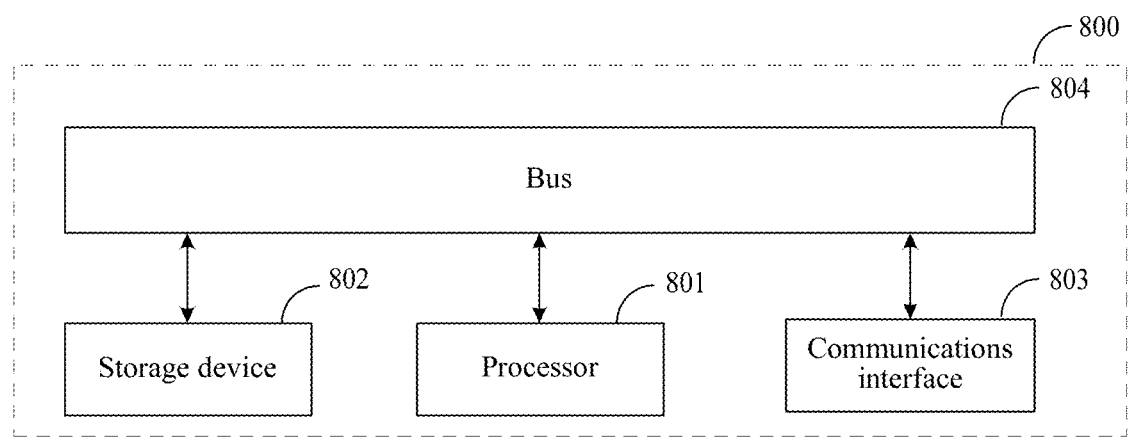
FIG. 8 is a schematic diagram of a terminal according to an embodiment of the present invention.

FIG. 8 is a schematic diagram of a terminal according to an embodiment of the present invention. As shown in FIG. 8, the terminal 800 according to this embodiment of the present invention includes a processor 801 coupled to one or more storage devices, a storage device 802, a communications interface 803, and a bus 804.

The processor 801 is a control center of the terminal 800 and provides sequencing and processing facilities to execute an instruction, perform an interrupt operation, and provide a timing function and many other functions. Optionally, the processor 801 includes one or more central processing units (CPU). Optionally, the terminal device 800 includes more than one processor. The processor 801 may be a single-core (single-CPU) processor or a multi-core (multi-CPU) processor. The term "processor" used in this specification refers to one or more devices, circuits, and/or processing kernels configured to process data such as a computer program instruction.

The storage device 802 may include a storage medium and a memory unit. The storage medium may be read-only such as a read-only memory (ROM), or be readable/writable such as a hard disk or flash memory. The memory unit may be a random access memory (RAM). Physically, the memory unit may be integrated with the processor 801, or integrated into the processor 801, or constructed in one or more independent units.

The processor 801 may execute program code stored in the storage device 802. Optionally, the program code stored in the storage medium of the storage device 802 may be replicated into the memory unit, so as to be executed by the processor. The processor may execute at least one kernel, for example, a kernel in an operating system sold with a trademark such as LINUZ™, UNIX™, WINDOWS™, ANDROID™, or IOS™, and it is well known that the kernel is configured to control operations of the terminal device 800 by controlling execution of other programs or processes, controlling communication with a peripheral, and controlling use of resources of a calculating device.

The terminal device 800 further includes the communications interface 803, configured to communicate with another device or system directly or by using an external network.

The foregoing elements of the terminal device 800 may be coupled to each other by using any one of or any combination of the bus 804 such as a data bus, an address bus, a control bus, an extended bus or a local bus.

Optionally, the terminal device 800 further includes an output device and an input device (not shown in FIG. 8). The output device is coupled to the processor 801, and can display information in one or more manners. An example of the output device is a visual display device, for example, a crystal liquid display (LCD), a light emitting diode (LED) display, a cathode-ray tube (CRT), or a projector. The input device is also coupled to the processor 801, and can receive a user input of the terminal device 800 in one or more manners. An example of the input device includes a mouse, a keyboard, a touchscreen device, a sensing device, or the like.

The processor 801 reads the program code and data that are stored in the storage device 802 to perform the following operations:

obtaining first biometric feature information of a measured target, where the first biometric feature information includes a pulse wave signal and/or an electrocardio signal of the measured target;

obtaining a first status of the measured target according to the first biometric feature information, where the first status includes at least one of an activity status of the measured target, a posture of the measured target, or a measurement location of a pulse wave of the measured target;

determining a blood pressure calculation policy of the measured target according to the first status; and determining a blood pressure value of the measured target according to the blood pressure calculation policy and the first biometric feature information.

Further, in this embodiment of the present invention, the first biometric feature information of the measured target further includes:

an acceleration signal and/or an angular velocity signal of the measured target.

In this embodiment of the present invention, the processor 801 is further configured to: if the terminal is calibrated when the measured target is in the first status, determine that the blood pressure calculation policy of the measured target is a calibrated blood pressure calculation policy; or the processor 801 is further configured to: if the terminal is uncalibrated when the measured target is in the first status, determine that the blood pressure calculation policy of the measured target is an uncalibrated blood pressure calculation policy.

In this embodiment of the present invention, the processor 801 is further configured to determine a calibrated blood pressure calculation model and a calibration parameter corresponding to the first status in the calibrated blood pressure calculation model.

In this embodiment of the present invention, the processor 801 is further configured to determine a first calibrated blood pressure calculation model according to the first status.

In this embodiment of the present invention, the calibrated blood pressure calculation model is:

$$DBP = \frac{SBP_0}{3} + \frac{2DBP_0}{3} + A\ln\left(\frac{PTT_0}{PTT}\right) - \frac{(SBP_0 - DBP_0)}{3}\frac{PTT^2}{PTT_0^2} \quad (3)$$

$$SBP = DBP + (SBP_0 - DBP_0)\frac{PTT_0^2}{PTT^2}, \quad (4)$$

where

SBP is systolic blood pressure; DBP is diastolic blood pressure; PTT is a pulse wave transmission time; A is a blood pressure calculation coefficient; and $SBP_0$, $DBP_0$, and $PTT_0$ are calibration parameters in the calibrated blood pressure calculation model.

In this embodiment of the present invention, the processor 801 is further configured to: before the terminal obtains the first biometric feature information of the measured target, calibrate the terminal, where the processor that calibrates the terminal is specifically configured to:

obtain second biometric feature information of the measured target, where the second biometric feature information includes a pulse wave signal and/or an electrocardio signal of the measured target;

obtain a second status of the measured target according to the second biometric feature information, where the second status includes at least one of an activity status of the measured target, a posture of the measured target, or a measurement location of a pulse wave of the measured target;

obtain a standard blood pressure value when the measured target is in the second status; and determine, according to the standard blood pressure value and the second biometric feature information, a calibration parameter corresponding to the second status in the calibrated blood pressure calculation model.

In this embodiment of the present invention, the processor 801 is further configured to determine an uncalibrated blood pressure calculation model and a body parameter of the measured target, where the body parameter of the measured target includes at least one of age, gender, height, or weight.

In this embodiment of the present invention, the uncalibrated blood pressure calculation model is:

SBP=$A_1$ ln PTT+$A_2$Age+$A_3$Hei+$A_4$Wei+$A_5$Gen+$A_6$ ln Z+$A_7$ (1)

DBP=$B_1$ ln PTT+$B_2$Age+$B_3$Hei+$B_4$Wei+$B_5$Gen+$B_6$ ln Z+$B_7$ (2), where SBP is systolic blood pressure; DBP is diastolic blood pressure; $A_1$, $A_2$, $A_3$, $A_4$, $A_5$, $A_6$, and $A_7$ are systolic blood pressure calculation coefficients; $B_1$, $B_2$, $B_3$, $B_4$, $B_5$, $B_6$, and $B_7$ are diastolic blood pressure calculation coefficients; PTT is a pulse wave transmission time; Age is the age of the measured target; Hei is the height of the measured target; Wei is the weight of the measured target; Gen is the gender of the measured target; and Z is a pulse wave feature parameter.

In this embodiment of the present invention, the activity status of the measured target includes a moving state or a static state, and the processor 801 is further configured to determine the activity status of the measured target according to the acceleration signal and/or the angular velocity signal of the measured target;

the measurement location of the pulse wave includes a left limb or a right limb; and the processor 801 is further configured to determine the measurement location of the pulse wave according to a feature of a reference point of the electrocardio signal, or according to an acceleration and/or an angular velocity of the measured target, or according to an amplitude of the pulse wave signal of the measured target; and the posture of the measured target includes at least one of a sitting posture, a standing posture, a squatting posture, or a lying posture, and the processor 801 is further configured to determine the posture of the measured target according to the acceleration signal and/or the angular velocity signal of the measured target, and/or a feature of the pulse wave signal of the measured target.

When the terminal 800 according to this embodiment of the present invention is a wearable device, the wearable device includes an electrocardio signal collection apparatus and a pulse wave signal collection apparatus. The processor 801 controls the electrocardio signal collection apparatus and the pulse wave signal collection apparatus to obtain an electrocardio signal and a pulse wave signal.

Optionally, when the terminal device 800 according to this embodiment of the present invention is a general computing device or an application-specific computing device, such as a desktop computer, a notebook computer, a network server, a personal digital assistant (PDA), a mobile phone, a tablet computer, a wireless terminal device, a telecommunication device, an embedded system, or any other device having a structure similar to a structure shown in FIG. 8, the processor 801 of the terminal device 800 needs to include a wearable device including a electrocardio signal collection apparatus and a pulse wave signal collection apparatus, that is, the processor 801 controls the electrocardio signal collection apparatus and the pulse wave signal collection apparatus in the wearable device.

The terminal according to this embodiment of the present invention can increase precision of high blood pressure measurement. In addition, the terminal has a small volume and is easily operated.

The embodiments of the present invention provide a blood pressure measurement method, a blood pressure meter, and a terminal. The blood pressure meter obtains a first status of a measured target according to first biometric feature information of the measured target, determines a blood pressure calculation policy of the measured target according to the first status of the measured target, and determines a blood pressure value of the measured target according to the blood pressure calculation policy and the first biometric feature information. By means of the blood pressure measurement method and the blood pressure meter in the embodiments of the present invention, impact of a biometric feature and a state of a measured target on blood pressure is considered during blood pressure measurement, and an appropriate blood pressure calculation policy is selected to determine a blood pressure value of the measured target, thereby increasing precision of the blood pressure measurement.

A system embodiment basically corresponds to a method embodiment. For related parts, refer to the parts in the method embodiment. The described system embodiment is merely an example. The units described as separate parts may or may not be physically separate, and parts displayed as units may or may not be physical units, may be located in one position, or may be distributed on a plurality of network units. Some or all the modules may be selected according to actual needs to achieve the objectives of the solutions of the embodiments. A person of ordinary skill in the art may understand and implement the embodiments of the present invention without creative efforts.

The present invention can be described in the general context of executable computer instructions executed by a computer, for example, a program module. Generally, the program unit includes a routine, program, object, component, data structure, and the like for executing a particular task or implementing a particular abstract data type. The present invention may also be practiced in distributed calculating environments in which tasks are performed by remote processing devices that are connected through a communications network. In a distributed calculating environment, program modules may be located in both local and remote computer storage media including storage devices.

A person of ordinary skill in the art may understand that all or a part of the steps of the method embodiments may be implemented by a program instructing related hardware. The program may be stored in a computer readable storage medium, such as a ROM, a RAM, a magnetic disk, or an optical disc.

It should be noted that in this specification, relational terms such as first and second are only used to distinguish one entity or operation from another, and do not necessarily require or imply that any actual relationship or sequence exists between these entities or operations. Moreover, the terms "include", "comprise", or their any other variant is intended to cover a non-exclusive inclusion, so that a process, a method, an article, or an apparatus that includes a list of elements not only includes those elements but also includes other elements which are not expressly listed, or further includes elements inherent to such process, method, article, or apparatus. An element preceded by "includes a . . . " does not, without more constraints, preclude the existence of additional identical elements in the process, method, article, or apparatus that includes the element.

In short, the foregoing descriptions are merely examples of embodiments of the present invention, but are not intended to limit the protection scope of the present invention. Specific examples are used in this specification to describe the principle and implementation manners of the present invention. The descriptions of the foregoing embodiments are merely intended to help understand the method and core idea of the present invention. In addition, a person skilled in the art may, according to the idea of the present invention, make modifications with respect to the specific implementation manners and the application scope. Therefore, the content of this specification shall not be construed as a limitation to the present invention. Therefore, the content of this specification shall not be construed as a limitation to the present invention. Any modification, equivalent replacement, or improvement made without departing from the spirit and principle of the present invention shall fall within the protection scope of the present invention.

What is claimed is:

1. A blood pressure measurement terminal, wherein the terminal comprises at least one processor, a storage device, and a communications interface, wherein:
the storage device is configured to store computer-executable program code;
the at least one processor, the storage device, and the communications interface communicate with each other by using a bus; and
the at least one processor reads the program code and data that are stored in the storage device to perform the following operations:
obtaining first biometric feature information of a measured target, wherein the first biometric feature information comprises one or more of a pulse wave signal or an electrocardio signal of the measured target;

determining a first status of the measured target according to the first biometric feature information, wherein the first status comprises an activity status of the measured target, a posture of the measured target, and a measurement location of a pulse wave of the measured target;

determining a blood pressure calculation policy of the measured target according to the first status, wherein the determining of the blood pressure calculation policy includes determining a blood pressure calculation model and one or more coefficients for computing a blood pressure corresponding to the determined first status of the measured target; and determining a blood pressure value of the measured target according to the blood pressure calculation policy and the first biometric feature information.

2. The terminal according to claim 1, wherein the first biometric feature information of the measured target further comprises one or more of:

an acceleration signal or an angular velocity signal of the measured target.

3. The terminal according to claim 2, wherein the operations further comprise: if the terminal is calibrated when the measured target is in the first status, determining that the blood pressure calculation policy of the measured target is a calibrated blood pressure calculation policy.

4. The terminal according to claim 3, wherein the operations further comprise determining a calibrated blood pressure calculation model and a calibration parameter corresponding to the first status in the calibrated blood pressure calculation model.

5. The terminal according to claim 4, wherein the operations further comprise determining a first calibrated blood pressure calculation model according to the first status.

6. The terminal according to claim 4, wherein the calibrated blood pressure calculation model is:

$$DBP = \frac{SBP_0}{3} + \frac{2DBP_0}{3} + A\ln\left(\frac{PTT_0}{PTT}\right) - \frac{(SBP_0 - DBP_0)}{3}\frac{PTT^2}{PTT_0^2}$$

$$SBP = DBP + (SBP_0 - DBP_0)\frac{PTT_0^2}{PTT^2},$$

wherein

SBP is systolic blood pressure; DBP is diastolic blood pressure; PTT is a pulse wave transmission time; A is a blood pressure calculation coefficient; and $SBP_0$, $DBP_0$, and $PTT_0$ are calibration parameters in the calibrated blood pressure calculation model.

7. The terminal according to claim 1, wherein the operations further comprise: if the terminal is calibrated when the measured target is in the first status, determining that the blood pressure calculation policy of the measured target is a calibrated blood pressure calculation policy.

8. The terminal according to claim 7, wherein the operations further comprise determining a calibrated blood pressure calculation model and a calibration parameter corresponding to the first status in the calibrated blood pressure calculation model.

9. The terminal according to claim 8, wherein the operations further comprise determining a first calibrated blood pressure calculation model according to the first status.

10. The terminal according to claim 8, wherein the calibrated blood pressure calculation model is:

$$DBP = \frac{SBP_0}{3} + \frac{2DBP_0}{3} + A\ln\left(\frac{PTT_0}{PTT}\right) - \frac{(SBP_0 - DBP_0)}{3}\frac{PTT^2}{PTT_0^2}$$

$$SBP = DBP + (SBP_0 - DBP_0)\frac{PTT_0^2}{PTT^2},$$

wherein

SBP is systolic blood pressure; DBP is diastolic blood pressure; PTT is a pulse wave transmission time; A is a blood pressure calculation coefficient; and $SBP_0$, $DBP_0$, and $PTT_0$ are calibration parameters in the calibrated blood pressure calculation model.

11. The terminal according to claim 8, wherein the operations further comprise: before the terminal obtains the first biometric feature information of the measured target, calibrating the terminal, wherein calibrating the terminal comprises:

obtaining second biometric feature information of the measured target, wherein the second biometric feature information comprises at least one of a pulse wave signal or an electrocardio signal of the measured target;

obtaining a second status of the measured target according to the second biometric feature information, wherein the second status comprises at least one of an activity status of the measured target, a posture of the measured target, or a measurement location of a pulse wave of the measured target;

obtaining a standard blood pressure value when the measured target is in the second status; and determining, according to the standard blood pressure value and the second biometric feature information, a calibration parameter corresponding to the second status in the calibrated blood pressure calculation model.

12. The terminal according to claim 1, wherein the operations further comprise: if the terminal is uncalibrated when the measured target is in the first status, determining that the blood pressure calculation policy of the measured target is an uncalibrated blood pressure calculation policy.

13. The terminal according to claim 12, wherein the operations further comprise determining an uncalibrated blood pressure calculation model and a body parameter of the measured target, wherein the body parameter of the measured target comprises at least one of age, gender, height, or weight.

14. The terminal according to claim 13, wherein the uncalibrated blood pressure calculation model is:

SBP=$A_1$ ln PTT+$A_2$Age+$A_3$Hei+$A_4$Wei+$A_5$Gen+$A_6$ ln Z+$A_7$

DBP=$B_1$ ln PTT+$B_2$Age+$B_3$Hei+$B_4$Wei+$B_5$Gen+$B_6$ ln Z+$B_7$, wherein

SBP is systolic blood pressure; DBP is diastolic blood pressure; $A_1$, $A_2$, $A_3$, $A_4$, $A_5$, $A_6$, and $A_7$ are systolic blood pressure calculation coefficients; $B_1$, $B_2$, $B_3$, $B_4$, $B_5$, $B_6$, and $B_7$ are diastolic blood pressure calculation coefficients; PTT is a pulse wave transmission time; Age is the age of the measured target; Hei is the height of the measured target; Wei is the weight of the measured target; Gen is the gender of the measured target; and Z is a pulse wave feature parameter.

15. The terminal according to claim 1, wherein the activity status of the measured target comprises a moving state or a static state, and the operations further comprise determining the activity status of the measured target according to one or more of an acceleration signal or an angular velocity signal of the measured target;

the measurement location of the pulse wave comprises a left limb or a right limb; and operations further comprise determining the measurement location of the pulse wave according to a feature of a reference point of the electrocardio signal, or according to one or more of an acceleration or an angular velocity of the measured target, or according to an amplitude of the pulse wave signal of the measured target; and the posture of the measured target comprises at least one of a sitting posture, a standing posture, a squatting posture, or a lying posture, and the operations further comprise determining the posture of the measured target according to one or more of the acceleration signal or the angular velocity signal of the measured target, or a feature of the pulse wave signal of the measured target.

16. The terminal of claim 1, wherein the terminal comprises a visual display device and wherein the operations further comprise providing information for display on the visual display device of the terminal.

17. A computer-implemented method performed by a blood pressure measurement terminal, comprising the steps of:
obtaining first biometric feature information of a measured target, wherein the first biometric feature information comprises one or more of a pulse wave signal or an electrocardio signal of the measured target;
determining a first status of the measured target according to the first biometric feature information, wherein the first status comprises at least one of an activity status of the measured target, a posture of the measured target, or a measurement location of a pulse wave of the measured target;
determining a blood pressure calculation policy of the measured target according to the first status, wherein the determining of the blood pressure calculation policy includes determining a blood pressure calculation model for computing a blood pressure corresponding to the determined first status of the measured target; and
determining a blood pressure value of the measured target according to the blood pressure calculation policy and the first biometric feature information; and
wherein the first biometric feature information of the measured target further comprises one or more of:
an acceleration signal or an angular velocity signal of the measured target.

18. The method according claim 17, wherein determining a blood pressure calculation policy of the measured target according to the first status comprises:
if the terminal is calibrated when the measured target is in the first status, determining that the blood pressure calculation policy of the measured target is a calibrated blood pressure calculation policy.

19. The method according claim 17, wherein determining a blood pressure calculation policy of the measured target according to the first status comprises:
if the terminal is uncalibrated when the measured target is in the first status, determining that the blood pressure calculation policy of the measured target is an uncalibrated blood pressure calculation policy.

20. The method of claim 17, further comprising the step of providing information for display on a visual display device of the terminal.

21. A non-transitory, computer-readable storage medium comprising instructions which, when executed by a computer, cause the computer to perform the steps of:
obtaining first biometric feature information of a measured target, wherein the first biometric feature information comprises one or more of a pulse wave signal or an electrocardio signal of the measured target;
determining a first status of the measured target according to the first biometric feature information, wherein the first status comprises an activity status of the measured target, a posture of the measured target, and a measurement location of a pulse wave of the measured target;
determining a blood pressure calculation policy of the measured target according to the first status, wherein the determining of the blood pressure calculation policy includes determining a blood pressure calculation model and one or more coefficients for computing a blood pressure corresponding to the determined first status of the measured target; and
determining a blood pressure value of the measured target according to the blood pressure calculation policy and the first biometric feature information; and
wherein the first biometric feature information of the measured target further comprises one or more of:
an acceleration signal or an angular velocity signal of the measured target.

22. The non-transitory computer-readable storage medium according claim 21, wherein determining a blood pressure calculation policy of the measured target according to the first status comprises:
if the computer is calibrated when the measured target is in the first status, determining that the blood pressure calculation policy of the measured target is a calibrated blood pressure calculation policy, or
if the computer is uncalibrated when the measured target is in the first status, determining that the blood pressure calculation policy of the measured target is an uncalibrated blood pressure calculation policy.

23. The non-transitory computer readable medium of claim 21, wherein the instructions which, when executed by the computer, cause the computer to perform the step of providing information for display on a visual display device of a blood pressure measurement terminal.

* * * * *

UNITED STATES PATENT AND TRADEMARK OFFICE
CERTIFICATE OF CORRECTION

| | |
|---|---|
| PATENT NO. | : 11,564,640 B2 |
| APPLICATION NO. | : 15/762640 |
| DATED | : January 31, 2023 |
| INVENTOR(S) | : Wenjuan Chen and Yu Zhu |

It is certified that error appears in the above-identified patent and that said Letters Patent is hereby corrected as shown below:

In the Claims

In Column 27, Line 48, in Claim 18, after "according" insert -- to --.

In Column 28, Line 1, in Claim 19, after "according" insert -- to --.

In Column 28, Line 38, in Claim 22, after "according" insert -- to --.

Signed and Sealed this
Ninth Day of May, 2023

Katherine Kelly Vidal
*Director of the United States Patent and Trademark Office*